United States Patent [19]

Hammar

[11] 3,969,467

[45] July 13, 1976

[54] 12-ANTI AND SYN-(N-BENZYL-N-ALKYLAMINOMETHYL)-10,11-DIHYDRO-5,10-METHANO-5H-DIBENZO[a,d]CYCLOHEPTENES AND THE SALTS THEREOF

[75] Inventor: Walton James Hammar, St. Paul, Minn.

[73] Assignee: Riker Laboratories, Inc., Northridge, Calif.

[22] Filed: May 14, 1973

[21] Appl. No.: 360,105

[52] U.S. Cl. ............ 260/570.9; 260/459 R; 260/501.1; 260/515 R; 260/558 R; 260/562 P; 260/570.8 TC; 260/618 F; 260/649 R; 260/665 G; 424/316; 424/330; 260/544 B; 260/567.6 R

[51] Int. Cl.² .......................................... C07C 87/29

[58] Field of Search ............ 260/570.9, 649, 501.1, 260/57

[56] References Cited
OTHER PUBLICATIONS

Bohme et al., "Chemical Abstracts," vol. 54, pp. 4566–4567 (1960).
Cristol et al., "Journal Organic Chemistry," vol. 30, pp. 1956–1958 (1965).

*Primary Examiner*—Robert V. Hines
*Attorney, Agent, or Firm*—Alexander, Sell, Steldt & DeLaHunt

[57] ABSTRACT

10,11-Dihydro-12-(N,N-disubstitutedaminomethyl)-5,10-methano-5H-dibenzo[a,d]cycloheptenes are prepared by reacting the Grignard reagent of 10,11-dihydro-12-halo-5,10-methano-5H-dibenzo[a,d]cycloheptenes with alkyl ethers of N,N-disubstitutedaminomethyl alcohols. Some of the intermediates in this process are novel compounds.

2 Claims, No Drawings

12-ANTI AND SYN-(N-BENZYL-N-ALKYLAMINOMETHYL)-10,11-DIHYDRO-5,10-METHANO-5H-DIBENZO[A,D]CYCLOHEPTENES AND THE SALTS THEREOF

Background of the Invention

Compounds prepared by the process of the present invention are heretofore known dibenzo[a,d]cycloheptenes which have previously been reported as possessing useful pharmacologic activity on the central nervous system. The novel intermediate compounds of the present invention are useful in the process of the invention for preparing such amines. Pharmacologically active compounds prepared by the process of the invention are disclosed in German Offenlegungschrift No. (publication document) 2,216,884 and in my copending U.S. patent application Ser. No. 194,056 and now U.S. Pat. No. 3,860,652.

The German publication document describes a process which requires synthesis, from anthracene, of the compound 12-carboxy-10,11-dihydro-5,10-methano-5H-dibenzo[a,d]cycloheptene using several synthetic steps. This intermediate can also be prepared from 12-chloro-10,11-dihydro-5,10-methano-5H-dibenzo[a,d]cycloheptene as described in U.S. patent application Ser. No. 194,056. Both of the reference processes then proceed (1) to convert the 12-carboxy acid to the corresponding acid chloride, (2) react the acid chloride with a suitable amine to provide an amide, and (3) to reduce the amide with one of the relatively expensive and hazardous metal hydride-type reducing agents to the desired pharmacologically active products. Thus, the methods known to the art for the synthesis require starting with 12-chloro-10,11-dihydro-5,10-methano-5H-dibenzo[a,d]cycloheptane or the corresponding 12-carboxy compound.

It is the object of the present invention to provide a novel, less costly and efficient synthetic method for 10,11-dihydro-12-(N,N-disubstitutedaminomethyl)-5,10-methano-5H-dibenzo[a,d]cycloheptenes and the corresponding N-monosubstituted compounds.

Further objects of the invention will be apparent from the disclosure and the claims.

DETAILED DESCRIPTION OF THE INVENTION

This invention relates to a process for the preparation of compounds of Formula I

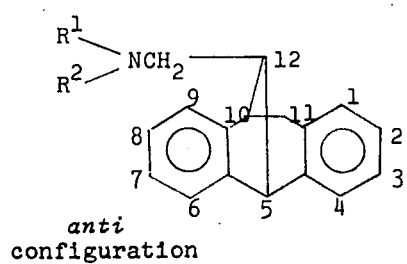

anti configuration

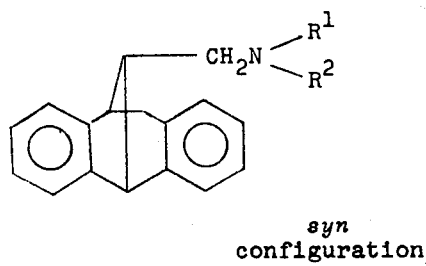

syn configuration

Formula I wherein $R^1$ is methyl or ethyl and $R^2$ is methyl, ethyl or benzyl, which comprises the steps of reacting a 10,11-dihydro-12-halo-5,10-methano-5H-dibenzo[a,d]cycloheptene wherein halo is bromo or chloro with magnesium to form the corresponding Grignard reagent and then adding to the Grignard reagent an ether of the formula

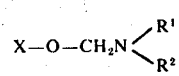

wherein X is straight or branched chain alkyl of one to eight carbon atoms. The product of Formula I is isolated from the reaction mixture.

"Halo" is presently preferred to be chloro.

This invention also relates to the process in an embodiment in which certain novel intermediate compounds of the invention are employed, wherein $R^2$ in the formula above is benzyl, which are particularly useful for preparing secondary amine compounds of Formula II which are active on the central nervous system

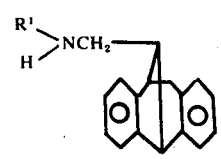

Formula II wherein $R^1$ is methyl or ethyl.

The invention also relates to the preparation of the compounds of Formula II by a process comprising reacting a 10,11-dihydro-12-halo-5,10-methano-5H-dibenzo[a,d] cycloheptene with magnesium to form the corresponding Grignard reagent, then reacting with a novel ether of the formula

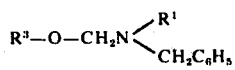

wherein $R^3$ is straight or branched chain alkyl of one to eight carbon atoms, and removing the benzyl group by reducing the product with hydrogen in the presence of palladium on charcoal. The product of Formula II is isolated from the reduction reaction.

It is apparent that the group

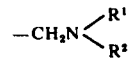

is bonded to position 12 of the 10,11-dihydro-5,10-methano-5H-dibenzo[a,d]cycloheptene system in one of two non-equivalent geometrically isomeric configurations, commonly termed anti or syn (as exemplified for Formula I). However, both of the geometrical forms have been reported to have central nervous system activity.

The process of the invention provides a method for obtaining both isomers. Both *syn* and *anti* isomers of 10,11-dihydro-12-chloro-5,10-methano-5H-dibenzo[a,d]cycloheptene are known starting materials. The desired isomer is readily obtained in essentially pure form by fractional recrystallization. The isomers of 12-bromo-10,11-dihydro-5,10-methano-5H-dibenzo[a,d]cycloheptene are believed to be unknown heretofore, but they can be synthesized from available starting materials. The novel bromo compound is prepared using the method described in the literature to prepare the *anti* chloro compound.

Alternatively, if pure isomers of compounds of Formula I are not desired, the starting material of the first step may be a mixture of stereoisomers and/or the product may be used as a mixture of stereoisomers.

The starting material 10,11-dihydro-12-halo-5,10-methano-5H-dibenzo[a,d]cycloheptene is reacted with magnesium to form the Grignard reagent under carefully controlled conditions, as typically used in this kind of reaction. Thus, the solvent is a well-dried ether such as diethyl ether, dioxane, di-n-butyl ether, or preferably tetrahydrofuran. The reaction is run under an inert atmosphere such as dry nitrogen. In order to facilitate the initiation of the Grignard reaction, the solvent such as tetrahydrofuran is treated and dried with a 70 percent solution of sodium bis(2-methoxyethoxy)aluminum hydride in benzene. Alternatively a catalytic quantity of a more reactive haloalkane, for example an iodoalkane such as ethyl iodide or a bromoalkane such as 1,2-dibromoethane or isopropyl bromide, may be used.

To initiate the Grignard reaction, it is preferred to heat the dried solvent, magnesium turnings and the 10,11-dihydro-12-halo-5,10-methano-5H-dibenzo[a,d]cycloheptene at reflux. Depending on the solvent used, the temperature of the reaction may range from about 35° to 150° C. When a reactive haloalkane is used to facilitate the formation of the Grignard reagent, the haloalkane and magnesium in the solvent are preferably heated at reflux until the reaction begins. Next the 10,11-dihydro-12-halo-5,10-methano-5H-dibenzo[a,d]cycloheptene is added, and refluxing is carried out for one or two hours or preferably up to twenty hours to maximize formation of the Grignard reagent.

Once the Grignard reagent is formed, the reaction mixture is allowed to cool to room temperature and the ether of formula

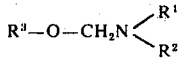

is added slowly. The reaction is exothermic and is allowed to proceed to completion.

The product is isolated by conventional methods. For example, the inorganic residue from the Grignard reaction is decomposed by known methods such as treatment with saturated ammonium chloride solution. The organic layer is separated, and the product is isolated and purified by extraction and/or recrystallization. If pure geometrical isomers are desired they are generally obtained conveniently by fractional crystallization.

Alternatively, the products may be isolated as acid addition or quaternary ammonium salt. The free base is dissolved in a suitable solvent such as an alcohol (for example isopropyl alcohol, treated with, for example, an acid to form the salt, and the solution is treated with an ether to facilitate precipitation of the acid addition salt.

Formation of the salt may simply be a purification step wherefrom the free base is re-isolated, or the salt may be useful, as such, as is known in the art. Salts with hydrochloric, sulfonic, nitric, benzoic, acetic, propionic, citric, phosphoric and the like acids can be prepared and used for isolation or other purposes as desired.

When $R^2$ benzyl, the product isolated from the reaction of the second step may be converted to a secondary amine, known to be pharmacologically useful, by removal of the benzyl group. It has been found that this reaction is readily achieved without much interference from side reactions by treating the benzyl-substituted compound with hydrogen at pressures of 2 to 4 atmospheres in the presence of catalytic amounts of palladium on charcoal.

The process of this invention is the presently preferred process for the preparation of 10,11-dihydro-12-*anti*-(N,N-dimethylaminomethyl)-5,10-methano-5H-dibenzo[-a,d]cycloheptene and thence its hydrochloride. This compound has received extensive testing in animals and has been found to be an active antidepressant agent with a favorable therapeutic ratio.

The N-benzyl-N-methyl or -ethylaminomethyl alkyl ethers used in the process of the invention are novel and useful intermediates. They are prepared by reaction of N-benzyl-N-methyl or -ethylamine with the selected alcohol and formaldehyde. The alcohols used to prepare these novel compounds are straight or branched chain alkanols having one to 20 carbon atoms. Presently preferred are those having two to eight carbon atoms. Surprisingly these N-benzyl alkylaminoalkyl ethers are stable for use in the method of the invention although the N-benzyl group is easily removed to give compounds of Formula II.

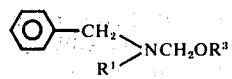

Formula III wherein $R^1$ and $R^3$ have the same significance as hereinabove represents these ethers.

The N,N-dimethylaminomethyl alkyl ethers are known compounds prepared by known methods, for example as described in J. Chem. Soc. 123, 536 (1923).

The following examples are provided to illustrate the presently preferred embodiments of the invention. They are not intended to limit the scope of the invention described and explained in the specification. All melting points and boiling points are uncorrected.

EXAMPLE 1

10,11-Dihydro-12-*anti*-(N,N-dimethylaminomethyl)-5,10-methano-5H-dibenzo[a,d]cycloheptene Into a dry 3 liter round bottom flask under a nitrogen atmosphere is placed magnesium turnings (32.2 g., 1.33 mole), dry tetrahydrofuran (125 ml.) and isopropyl bromide (4.3 ml.). The resulting mixture is stirred at reflux for one hour until the mixture turns dark brown.

Then, at refluxing temperature, a tetrahydrofuran (1.0 liter) solution of 12-*anti*-chloro-10,11-dihydro-5,10-methano-5H-dibenzo[a,d]cycloheptene (266 g., 1.11 mole) is added dropwise over 30 minutes. The resulting mixture is stirred at refluxing temperatures for 20 hours. The Grignard solution is cooled to room temperature, and then N,N-dimethylaminomethyl isobutyl ether (183.7 g., 1.40 mole) is added dropwise over one hour causing an exotherm to 55° C. The resulting mixture is stirred at refluxing temperature for 2.5 hours.

After cooling to room temperature, the reaction solution is poured into saturated ammonium chloride (1.5 liter) solution. The tetrahydrofuran layer is isolated and the solvent removed under vacuum. The resulting oil is dissolved in diethyl ether. The ether layer is washed with water and extracted with 10 percent hydrochloric acid. The acid layer is isolated and made basic to pH 10 by adding 50 percent sodium hydroxide solution. A solid forms. It is collected, washed with water and dried, giving 190 g. of 10,11-dihydro-12-(N,N-dimethylaminomethyl)-5,10-methano-5H-dibenzo[a,d]cycloheptene, m.p. 91°–95° C. The produce is about 80 percent *anti* isomer and 20 percent *syn* isomer according to nuclear magnetic resonance analysis. Pure *anti* isomer is obtained by fractional recrystallization from hexane.

EXAMPLE 2

To a solution of isobutanol (19.2 g., 0.26 mole) and N-benzyl-N-methylamine (30 g., 0.25 mole) is added excess 40 percent formaldehyde (25 g.). The mixture reacts exothermically, and two layers form. Potassium carbonate is added to form a saturated aqueous layer. The mixture is stirred overnight, then extracted thoroughly with diethyl ether. The ether layer is dried, then evaporated under vacuum to provide a residual oil. The residue is distilled under vacuum to provide N-benzyl-N-methylaminomethyl isobutyl ether, b.p. 72°–77° C. at 1.5 mm. Hg as a clear liquid. The structure is established by nuclear magnetic resonance analysis.

Using the method of Example 2 the following novel ethers are prepared:

TABLE I

| Ex. No. | Starting Alcohol | Starting Amine | Product |
|---|---|---|---|
| 3 | isobutanol | N-benzyl-N-ethyl-amine | N-benzyl-N-ethyl-aminomethyl isobutyl ether |
| 4 | ethanol | N-benzyl-N-methyl-amine | N-benzyl-N-methyl-aminomethyl ethyl ether |
| 5 | n-butanol | N-benzyl-N-methyl-amine | N-benzyl-N-methyl-aminomethyl butyl ether |
| 6 | n-octanol | N-benzyl-N-methyl-amine | N-benzyl-N-methyl-aminomethyl octyl ether |

EXAMPLE 7

Using the method of Example 1, 0.062 mole of the Grignard reagent of 12-*anti*-chloro-10,11-dihydro-5,10methano-5H-dibenzo[a,d]cycloheptene is prepared and added slowly to a solution of N-benzyl-N-methylaminomethyl isobutyl ether (18.7 g., 0.09 mole) in 85 ml. of tetrahydrofuran at about 25° C. The mixture is stirred and heated at reflux for 2 hours, cooled and treated with 66 ml. of saturated ammonium chloride solution. The mixture is concentrated under vacuum to remove the tetrahydrofuran; then the residue is extracted with diethyl ether. The ether extracts are dried, then evaporated to provide an oil which is 12-(N-benzyl-N-methylaminomethyl)-10,11-dihydro-5,10-methano-5H-dibenzo[a,d]cycloheptene.

A portion (3.3 g.) of the product is dissolved in 20 ml. of methanol and treated with 0.9 g. of oxalic acid in methanol (5 to 10 ml.). The solution is concentrated under vacuum to a syrup which is triturated with acetone to provide a white crystalline solid. The solid is separated by filtration and washed with acetone to give 12-(N-benzyl-N-methylaminomethyl)-10,11-dihydro-5,10-methano-5H-dibenzo[a,d]cycloheptene oxalate.

Alternatively the free base is reacted with hydrogen chloride in ether to provide 12-(N-benzyl-N-methylaminomethyl)-10,11-dihydro-5,10-methano-5H-dibenzo[a,d]cycloheptane hydrochloride, m.p. 98°–101° C. The structure of the product is confirmed through infrared and nuclear magnetic resonance spectral analysis.

Analysis: Calculated for $C_{25}H_{25}N.HCl.H_2O$: C, 76.2; H, 7.2; N, 3.6; Found: C, 76.4; H, 7.2; N, 3.7.

EXAMPLE 8

12-*anti*-(N-Benzyl-N-methylaminomethyl)-10,11-dihydro-5,10-methano-5H-dibenzo[a,d]cycloheptene (10 g., 0.0295 mole) is dissolved in 200 ml. of 95 percent ethanol; 3.5 g. of palladium on charcoal is added and the mixture is hydrogenated at about 25° C. under a hydrogen pressure of 45 p.s.i. on a Paar apparatus for about 2 hours. The mixture is filtered, and the filtrate is concentrated under vacuum. The residue is partitioned between an aqueous acid-diethyl ether mixture, and the ether layer is separated and discarded. The aqueous layer is basified, then extracted with ether. The ether layer is dried and concentrated under vacuum. The residue is again dissolved in ether, then treated with ethereal hydrogen chloride to form the hydrochloride salt of the product. The solid precipitate is separated by filtration and recrystallized from isopropyl alcohol. The identity of the product is established by its infrared and nuclear magnetic resonance spectra as 12-(N-methylaminomethyl)-10,11-dihydro-5,10-methano-5H-dibenzo[a,d]cycloheptene hydrochloride. The product is 23 percent *syn* isomer and 77 percent *anti* isomer according to the nuclear magnetic resonance spectral analysis of the free base in perdeutero-benzene.

EXAMPLE 9

To a solution of dibenzobicyclo[2.2.2]octadiene (4.0 g., 0.05 mole) in 80 ml. of dichloromethane is added bromine (3.2 g., 0.05 mole) in 10 ml. of carbon tetrachloride. The mixture is stirred for about 30 minutes and evaporated, then carbon tetrachloride is added, and the mixture is evaporated. This procedure is repeated thrice. The resulting oil solidifies, and the solid is triturated with hexane, giving a solid. This is recrystallized from hexane containing a small amount of benzene, m.p. 122°–124°C. A nuclear magnetic resonance spectral analysis of the product shows it to be known 11-*endo*-12-*syn*-dibromo-10,11-dihydro-5,10-methano-5H-dibenzo[a,d]cycloheptene.

The product is dissolved in 75 ml. of ethyl acetate containing 2 g. of sodium acetate, and palladium on charcoal (2 g.) is added. The mixture is treated with hydrogen gas at room temperature and 45 p.s.i. in a Paar apparatus for about 16 hours. The mixture is filtered, and the filtrate is evaporated under vacuum to dryness. The product is recrystallized from hexane to give *syn*-12-bromo-10,11-dihydro-5,10-methano-5H-dibenzo[a,d]cycloheptene, m.p. 127°–128° C.

Analysis: Calculated for $C_{16}H_{13}Br$: C, 67.4; H, 4.6; Found: C, 67.3, H, 4.6.

Using the method of Example 1, the Grignard reagent formed from 12-*anti*-chloro-10,11-dihydro-5,10-methano-5H-dibenzo[a,d]cycloheptene is reacted with various reactive ethers shown in the following table to provide the products shown.

TABLE II

| Ex. No. | Ether Reactant | Product |
|---|---|---|
| 10 | N-benzyl-N-ethylaminomethyl isobutyl ether | 12-(N-benzyl-N-ethylaminomethyl)-10,11-dihydro-5,10-methano-5H-dibenzo[a,d]cycloheptene |
| 11 | N-benzyl-N-methylaminomethyl ethyl ether | 12-(N-benzyl-N-methylaminomethyl)-10,11-dihydro-5,10-methano-5H-dibenzo[a,d]cycloheptene |
| 12 | N-benzyl-N-methylaminomethyl butyl ether | 12-(N-benzyl-N-methylaminomethyl)-10,11-dihydro-5,10-methano-5H-dibenzo[a,d]cycloheptene |
| 13 | N-benzyl-N-methylaminomethyl octyl ether | 12-(N-benzyl-N-methylaminomethyl)-10,11-dihydro-5,10-methano-5H-dibenzo[a,d]cycloheptene |
| 14 | N-ethyl-N-methylaminomethyl ethyl ether | 12-(N-ethyl-N-methylaminomethyl)-10,11-dihydro-5,10-methano-5H-dibenzo[a,d]cycloheptene |

EXAMPLE 15

To a mixture of magnesium (0.4 g., 17 mmoles) and tetrahydrofuran at reflux is added 0.2 g. of isopropyl bromide (to catalyze the initiation of the Grignard reaction). Then a solution of *syn*-12-bromo-10,11-dihydro-5,10-methano-5H-dibenzo[a,d]-cycloheptene (4.0 g., 14 mmoles) in tetrahydrofuran is added, and the mixture is maintained at its reflux temperature for about 16 hours. The mixture is allowed to cool to room temperature, and 5 g. of N,N-dimethylaminomethyl isobutyl ether are added. The mixture is heated to its reflux temperature and maintained at reflux for about 28 hours, then allowed to cool to room temperature. An aqueous solution of 3 g. of ammonium chloride is added and mixed thoroughly with the reaction mixture. The tetrahydrofuran is removed under vacuum, then diethyl ether is added. The layers are separated; the aqueous layer is discarded and the ether layer is washed with saturated sodium chloride solution. The ether layer is then extracted with dilute hydrochloric acid. The acid extracts are basified with 10 percent sodium hydroxide solution. The basic mixture is then extracted with diethyl ether; the ether extracts are washed with saturated sodium chloride, then dried. The ether solution is evaporated under vacuum to provide an oil which solidifies to 10,11-dihydro-2-(N,N-dimethylaminomethyl)-5,10-methano-5H-dibenzo[a,d]cycloheptene, a mixture of 65 percent *anti* isomer and 35 percent *syn* isomer according to nuclear magnetic resonance spectral analysis.

What is claimed is:

1. A syn and/or anti compound of the formula

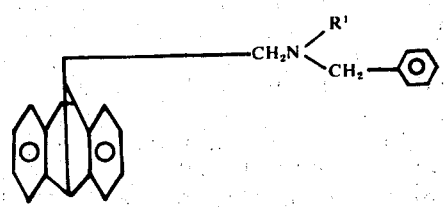

wherein $R^1$ is methyl or ethyl, and acid addition salts thereof.

2. A syn and/or anti compound of the formula

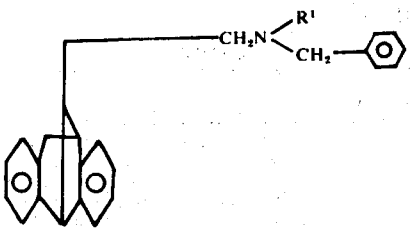

wherein $R^1$ is methyl or ethyl.

* * * * *